(12) United States Patent
Cheng et al.

(10) Patent No.: US 10,195,248 B2
(45) Date of Patent: *Feb. 5, 2019

(54) USE OF HAPTOGLOBIN SUBUNIT FOR PROMOTING WOUND HEALING

(71) Applicant: Taipei Medical University, Taipei (TW)

(72) Inventors: Tsai-Mu Cheng, Taipei (TW); Che-Chang Chang, Taipei (TW); TH Alexander Wu, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 63 days.

This patent is subject to a terminal disclaimer.

(21) Appl. No.: 15/371,233

(22) Filed: Dec. 7, 2016

(65) Prior Publication Data

US 2018/0036373 A1  Feb. 8, 2018

(30) Foreign Application Priority Data

Aug. 4, 2016 (TW) .............................. 105124779 A

(51) Int. Cl.
*A61K 38/00* (2006.01)
*A61K 38/17* (2006.01)

(52) U.S. Cl.
CPC ...... *A61K 38/1722* (2013.01); *A61K 38/1709* (2013.01)

(58) Field of Classification Search
None
See application file for complete search history.

(56) References Cited

U.S. PATENT DOCUMENTS 5,318,957 A * 6/1994 Cid .................... C07K 14/4717
514/13.3
9,260,497 B2 * 2/2016 Kim .................. C07K 14/4717

FOREIGN PATENT DOCUMENTS

WO    WO 2014/112702 A1 *  7/2014

* cited by examiner

*Primary Examiner* — Christina Bradley
(74) *Attorney, Agent, or Firm* — Locke Lord LLP; Tim Tingkang Xia, Esq.

(57) ABSTRACT

Provided is a method for promoting wound healing, which comprises: administering a haptoglobin subunit to a subject in need thereof. Also provided is a method for promoting wound healing, which comprises: administering a modified haptoglobin subunit to a subject in need thereof, the modified haptoglobin subunit comprising an amino acid sequence selected from one of SEQ ID NOs: 1-3.

5 Claims, 9 Drawing Sheets

Specification includes a Sequence Listing.

USE OF HAPTOGLOBIN SUBUNIT FOR PROMOTING WOUND HEALING

CROSS REFERENCE

The non-provisional application claims priority from Taiwan Patent Application NO. 105124779, filed on Aug. 4, 2016, the content thereof is incorporated by reference herein.

FIELD OF THE INVENTION

The present invention relates to pharmaceutical use of a haptoglobin (Hp) subunit, and particularly to, use of a haptoglobin subunit for promotion of wound healing.

BACKGROUND OF THE INVENTION

A wound is considered to be chronic if there is little or no sign for healing after an appropriate therapy for 6-8 weeks. A chronic wound is usually not caused by external force, as seen in an abrasion or a scald, but has latent factors to delay or obstruct its normal healing process. Common types of chronic wounds include a pressure ulcer, a decubitus ulcer, a leg ulcer, and a diabetic foot ulcer.

Poor wound healing partially results from a causal link between local infection and poor tissue blood perfusion. As the tissue has an oxygen content less than 20 mm-Hg, the wound healing process stops owing to the fact that this hypoxia makes proliferation of fibroblast cells, collagen production, and capillary angiogenesis retarded. Such hypoxia also inhibits anti-bacterial activity of neutrophils, and therefore aerobic bacteria breed quickly. At the same time, this hypoxia condition further leads to rapid growth of anaerobic bacteria. That is, the rapid growth of aerobic bacteria and anaerobic bacteria can make the wound worse.

SUMMARY OF THE INVENTION

A first aspect of the present invention is to provide a method for promoting wound healing, and the provided method comprises administering a haptoglobin subunit to a subject in need thereof.

In some embodiments, the haptoglobin subunit is present in form of a haptoglobin 1-1 protein, a haptoglobin 2-1 protein, or a haptoglobin 2-2 protein.

In other embodiments, the haptoglobin subunit is selected from a haptoglobin α1 subunit, a haptoglobin α2 subunit, or a haptoglobin β subunit.

In further embodiments, each haptoglobin protein is obtained via purification from blood, gene engineering, or chemical synthesis.

In certain embodiments, the haptoglobin subunit is obtained via purification from blood, gene engineering, or chemical synthesis.

In additional embodiments, the haptoglobin subunit has an anti-oxidant property and/or an anti-bacterial property.

In yet other embodiments, the wound is a chronic wound.

In still other embodiments, the chronic wound is selected from a pressure ulcer, a decubitus ulcer, a leg ulcer, or a diabetic foot ulcer.

A second aspect of the present invention is to provide a method for promoting wound healing, and the provided method comprises administering a modified haptoglobin subunit to a subject in need thereof, the modified haptoglobin subunit comprising an amino acid sequence selected from one of SEQ ID NOs: 1-3.

In some embodiments, the modified haptoglobin subunit is obtained via gene engineering or chemical synthesis.

In some embodiments, the haptoglobin subunit has an anti-oxidant property and/or an anti-bacterial property.

In other embodiments, the wound is a chronic wound.

In further embodiments, the chronic wound is selected from a pressure ulcer, a decubitus ulcer, a leg ulcer, or a diabetic foot ulcer.

The foregoing sequences of SEQ ID NOs: 1-3 are designed through substitution of Ala residues for some Cys residues in a native haptoglobin α1 subunit, α2 subunit, and β subunit, respectively. Accordingly, disulfide bond formation in the modified haptoglobin subunit can reduce so as to facilitate protein purification.

DETAILED DESCRIPTION OF THE INVENTION

The detailed description and preferred embodiment of the invention will be set forth in the following content, and provided for people skilled in the art so as to understand the characteristic of the invention.

Example 1

Cell Culture

Human umbilical vein endothelial cells (HUVECs) were purchased from the Bioresource Collection and Research Center (BCRC). All cells were cultured in a 10-cm culture dish coated with a layer of gelatin (0.25 mg/mL), and these cells were maintained in M199 medium supplemented with 20% fetal bovine serum (FBS), 100 U/mL of penicillin, 0.1 mg/mL of streptomycin, and 2 mmol/L L-glutamine at 37° C.

Example 2

Anti-Oxidant Test

In this experiment, production level of thiobarbituric acid-reactive substances (TBARS) was measured to determine oxidization level of low-density lipoproteins (LDL). Specifically, 1004, of each test article was mixed with 5 μM copper (II) sulfate ($CuSO_4$) and 20 μg of LDL, and then incubated at 37° C. for 2 hours. 250 μL of 20% tricholoroacetic acid was added to the precipitated protein. After that, 250 μL of 0.67% 2-thiobarbituric acid was added to the obtained mixture and incubated at 80° C. for 30 minutes. The final resultant was separated to give a supernatant by centrifugation at 3,000 g for 5 minutes. 300 μL of the supernatant was taken to a 96-well plate to measure its absorbance under 540 nm.

Figure 1:
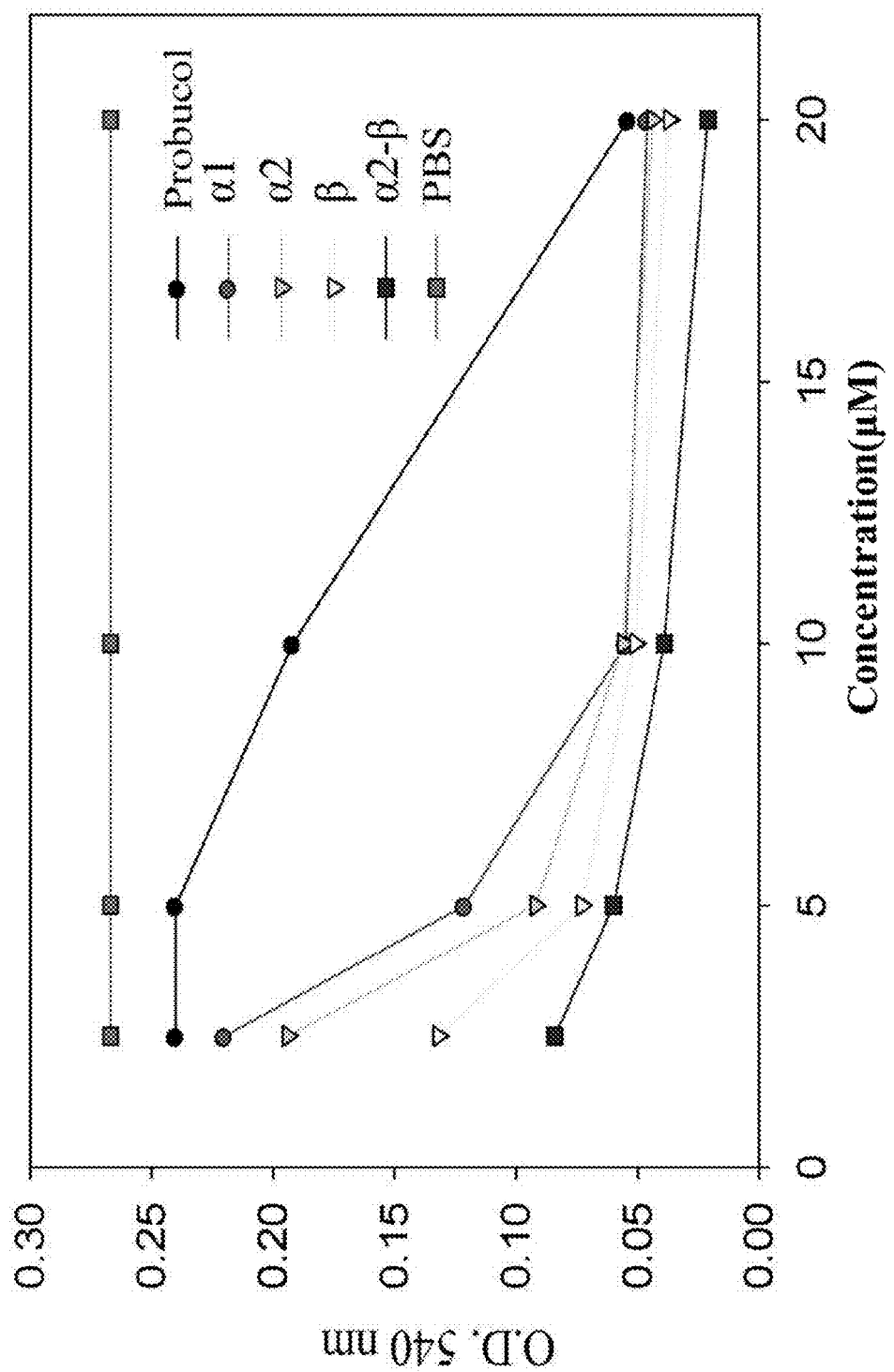
FIG. 1 is a curve diagram illustrating the anti-oxidant effect of various Hp subunits.

The result is shown in FIG. 1. Probucol is used as control, which is used for treatment of xanthoma and is a well-known powerful oxidant. An inhibitory concentration ($IC_{50}$) for anti-oxidant activity of an Hp α1 subunit is the greatest in all the test articles, and an Hp β subunit, an Hp 1-1 protein, and probucol follow it sequentially. That is, anti-oxidant activity of each Hp phenotype and each Hp subunit prevails against that of probucol.

Example 3

Scratch Assay

A scratch assay was used to determine wound healing. Specifically, HUVECs were seeded into a 6-well culture dish containing 0.5% FBS. When these cells grew to a confluent cell monolayer, a cell-free zone was formed by scratching the monolayer with the tip of a micropipette so as to mimic a wound. At the 0th, 2nd, 4th, and 8th hours after the cell culture at 37° C., an inverted microscope (Nikon TE 2000) was introduced to observe cell condition in each well.

Figure 2:
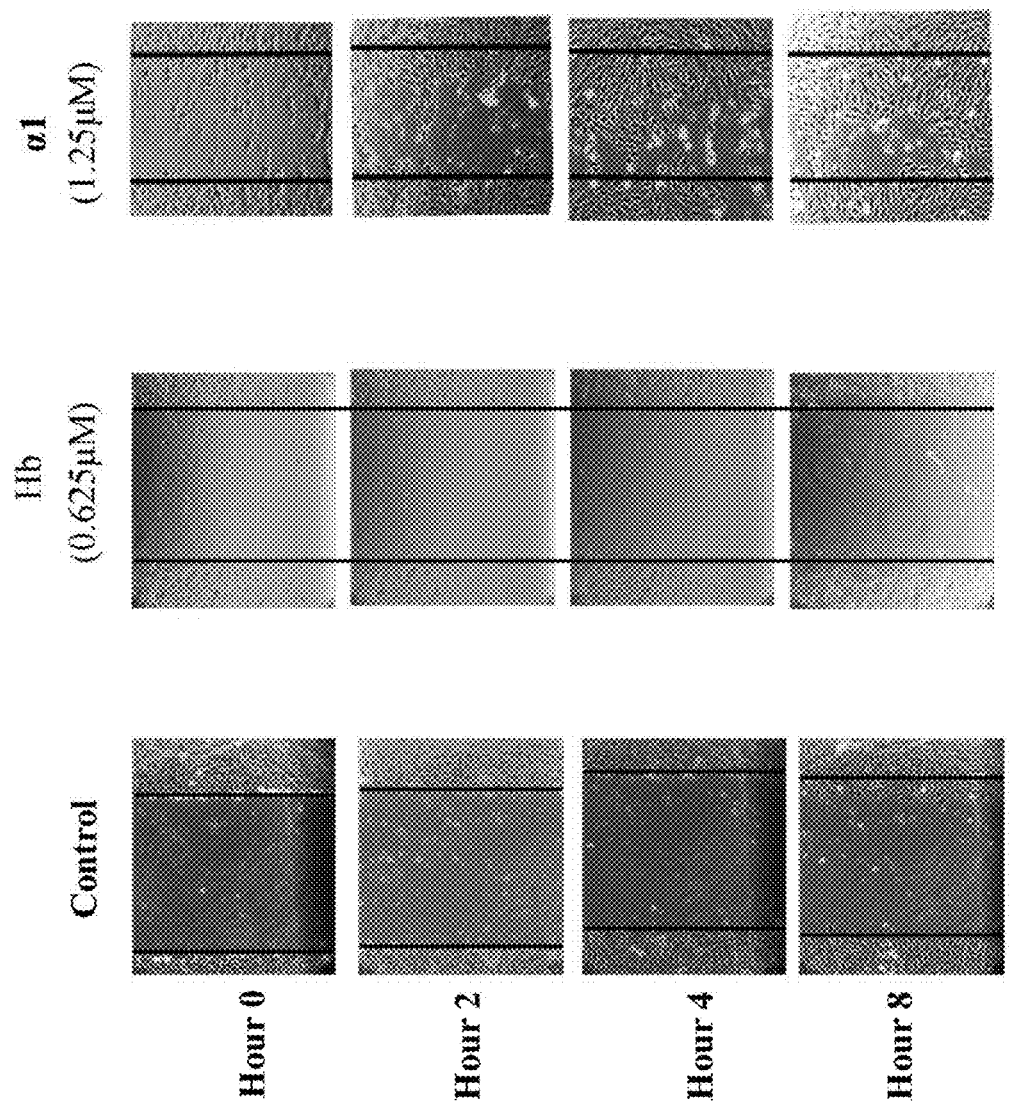
FIG. 2 is a picture showing the wound healing effect of an Hp α1 subunit in vitro.

The result is shown in FIG. 2. Compared with control HUVECs, Hp α1 subunit-treated HUVECs have a relatively obvious effect on wound healing at the 2nd, 4th, and 8th hours. In other words, each Hp subunit can promote cell migration and wound healing.

Example 4

Animal Experiment

In this experiment, two animal models of diabetes were established. For the first one, experimental mice were intraperitoneally injected with streptozotocin (STZ) at a dosage of 65 mg/kg per body weight. Since STZ has cytotoxicity to insulin-producing cells, it can induce these mice to suffer from diabetes. For the second one, experimental mice were fed with high-fat diets (HFD) to elevate their blood glucose concentrations. As such, diabetes was mimicked in these HFD-fed mice.

After three weeks, the blood glucose concentration of each mouse was measured by a blood glucose meter to confirm the STZ-injected mice and the HFD-fed mice indeed suffer from diabetes (TABLE 1). After anesthesia administration by injection with nembutal at a dosage of 65 mg/kg per body weight, a full thickness skin of each mouse's back was excised to form a wound. After which, different dressings were applied to the wounds, respectively. On the 0th, 4th, 7th, 11th, and 14th days after this application, each wound was photographed and its area size was calculated with ImageJ software.

TABLE 1

| | Control | | | | STZ | | | | HFD | | | |
|---|---|---|---|---|---|---|---|---|---|---|---|---|
| Blood glucose (mg/dL) | 110 | 117 | 167 | 124 | 199 | 206 | 224 | 208 | 220 | 197 | 251 | 249 |

Figure 3A:
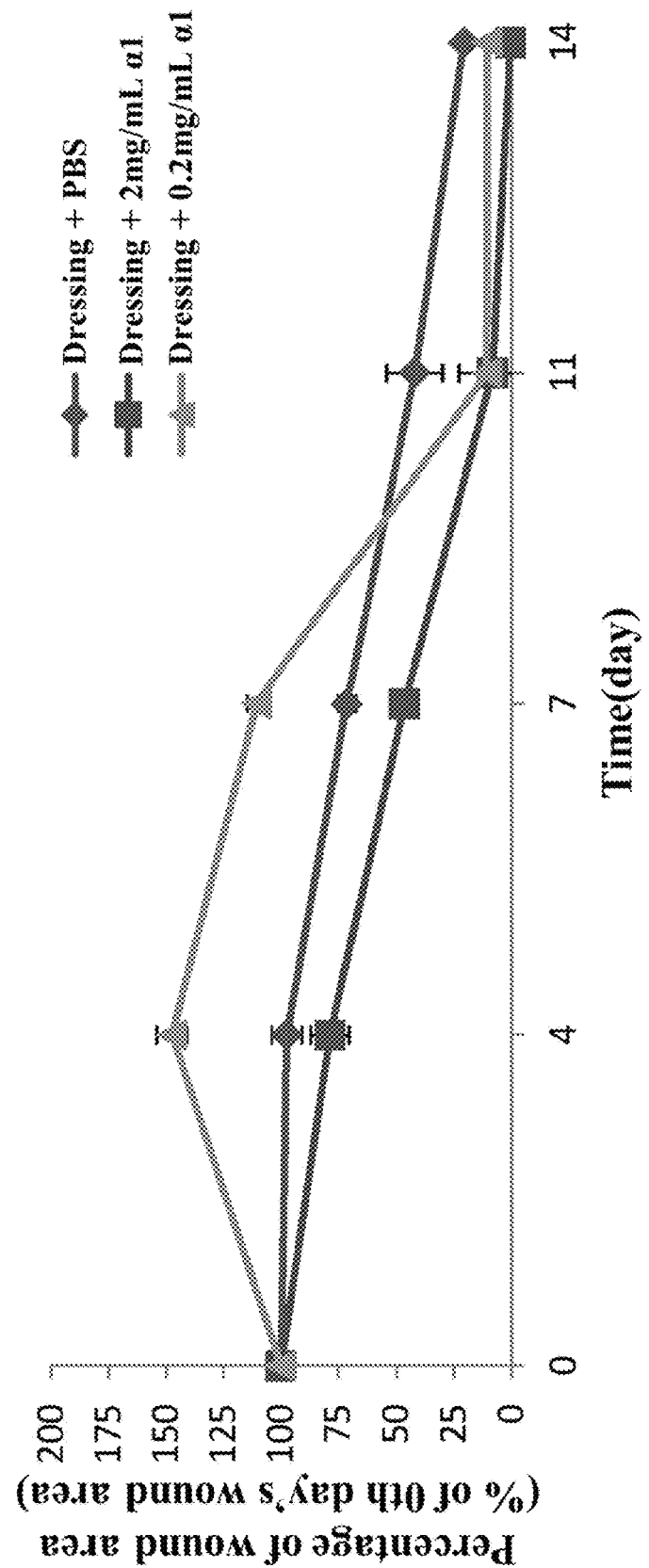
FIG. 3A is a curve diagram illustrating the wound area percentage of STZ-injected mice treated with various wound dressings.
Figure 3B:
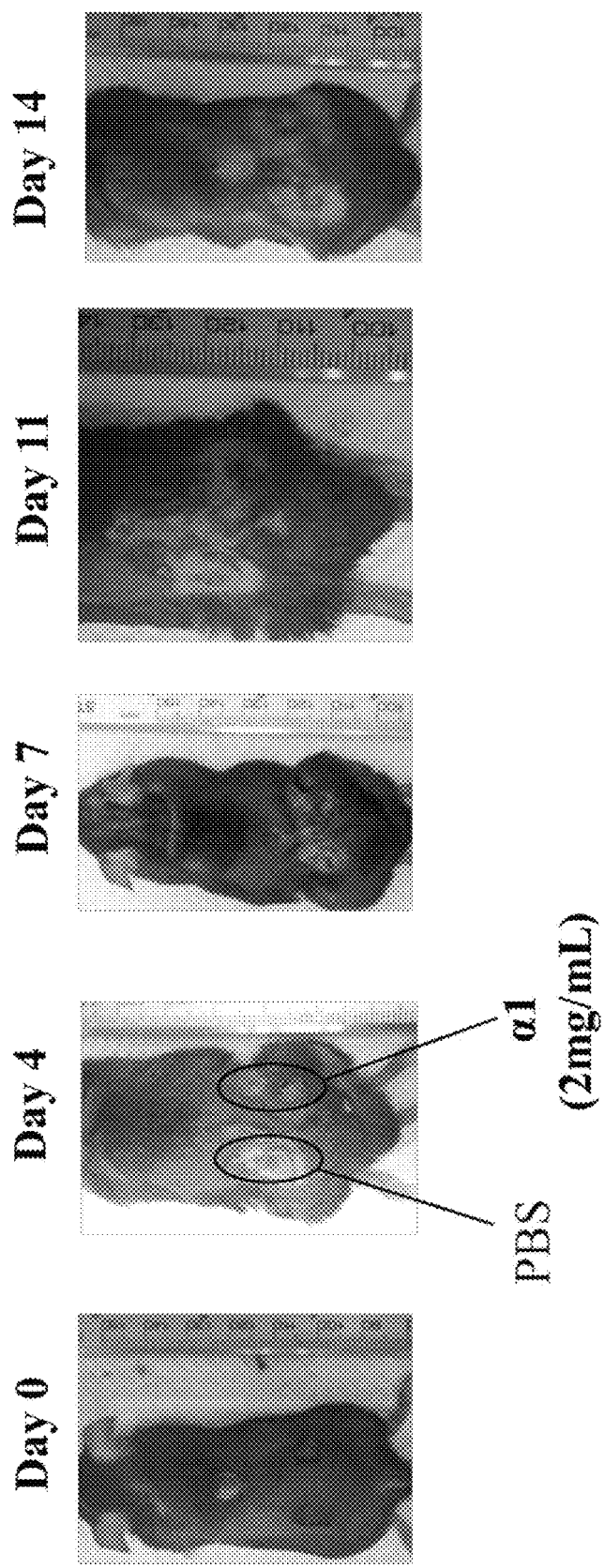
FIG. 3B is a picture showing the wounds of STZ-injected mice treated with various wound dressings.
Figure 4A:
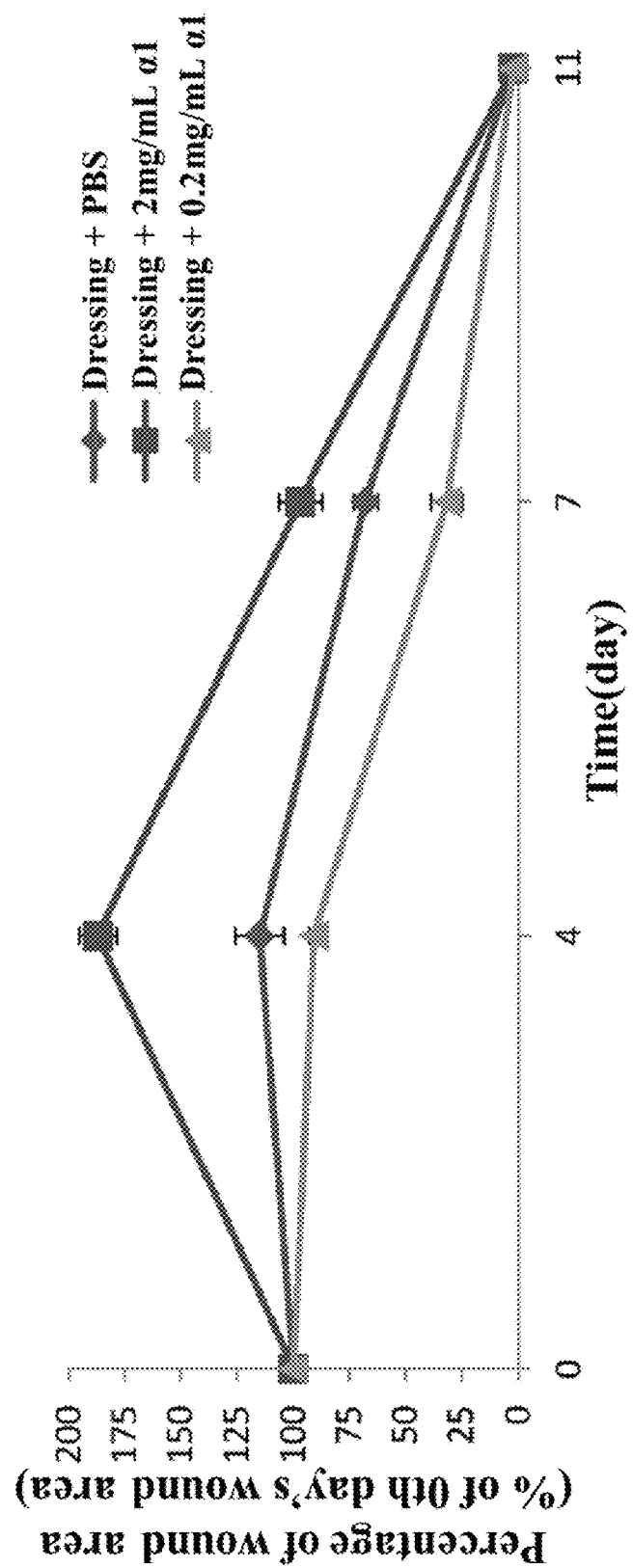
FIG. 4A is a curve diagram illustrating the wound area percentage of HFD-fed mice treated with various wound dressings.
Figure 4B:
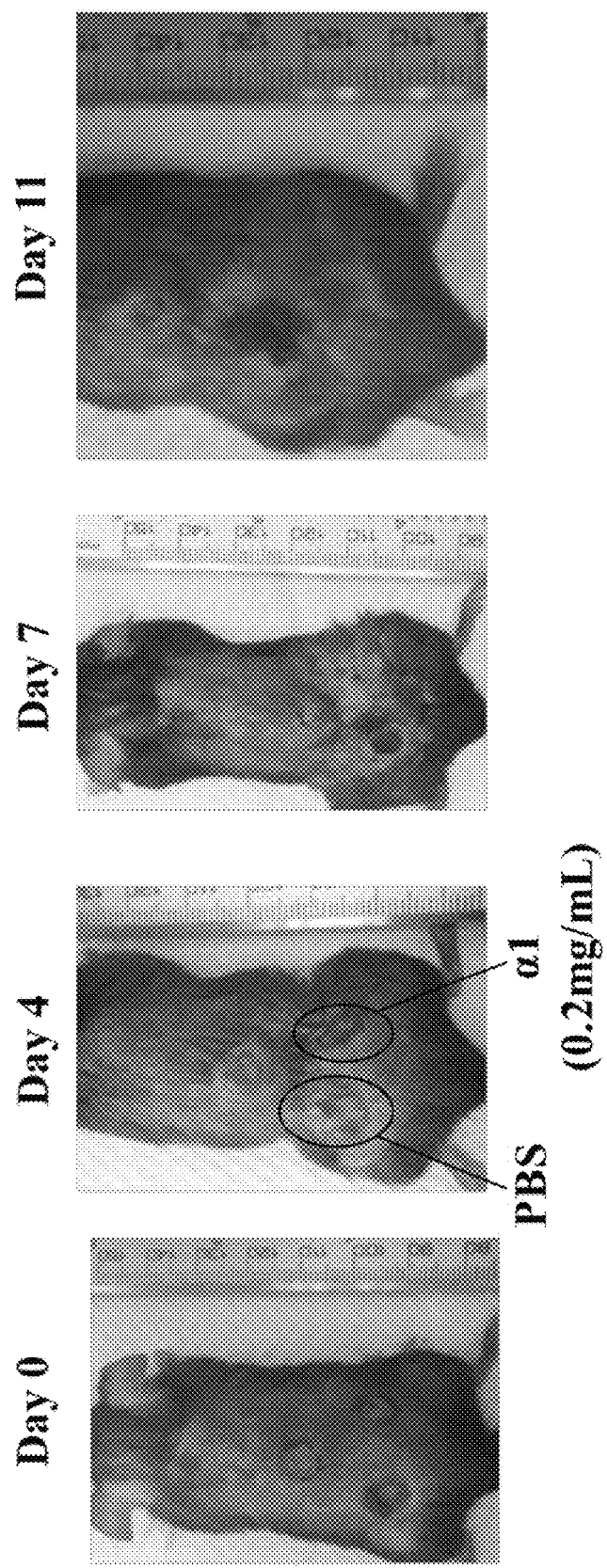
FIG. 4B a picture showing the wounds of HFD-fed mice treated with various wound dressings.

As shown in FIGS. 3A and 3B, the dressing containing 2 mg/mL of Hp al subunits can promote wound healing in the STZ-induced diabetic mouse model. In another aspect, the dressing containing 0.2 mg/mL of Hp α1 subunits can promote wound healing in the HFD-induced diabetic mouse model.

Example 5

Anti-Bacterial Test

This in vitro experiment was used to identify efficacy of test articles against *Clostridium difficile*, a gram-positive bacterium, and *Escherichia coli*, a gram-negative bacterium. Various Hp phenotypes were added to LB culture medium in various concentrations (100 μg/mL-200 μg/mL) so that the finally obtained medium has a volume of 1 mL. Ampicillin or penicillin/streptomycin was used as control, which is a well-known antibiotic. After incubation at 37° C. for various periods, absorbance under 600 nm of the medium was measured.

Figure 5:
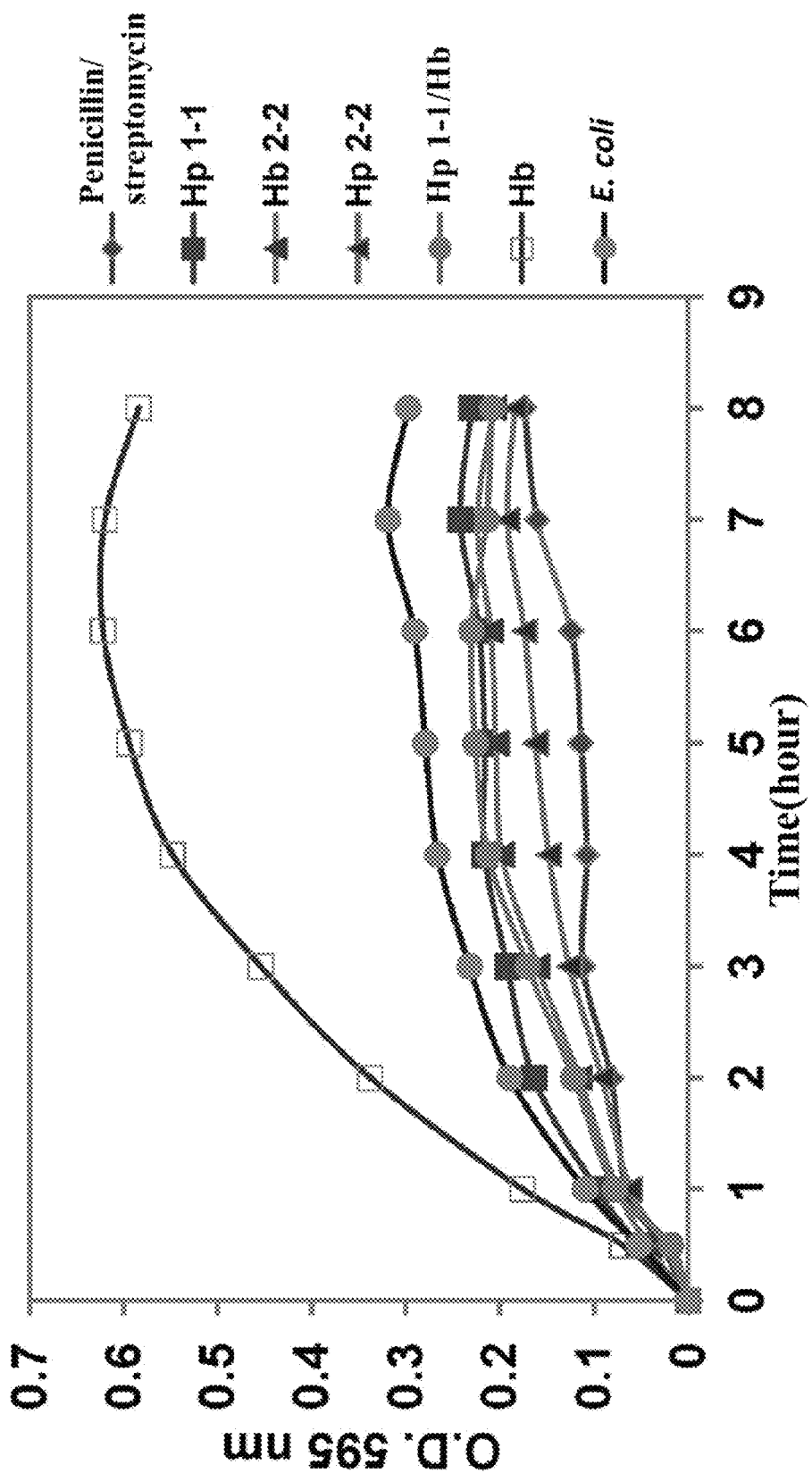
FIG. 5 is a curve diagram illustrating the effect of various Hp phenotypes against *Escherichia coli*.
Figure 6:
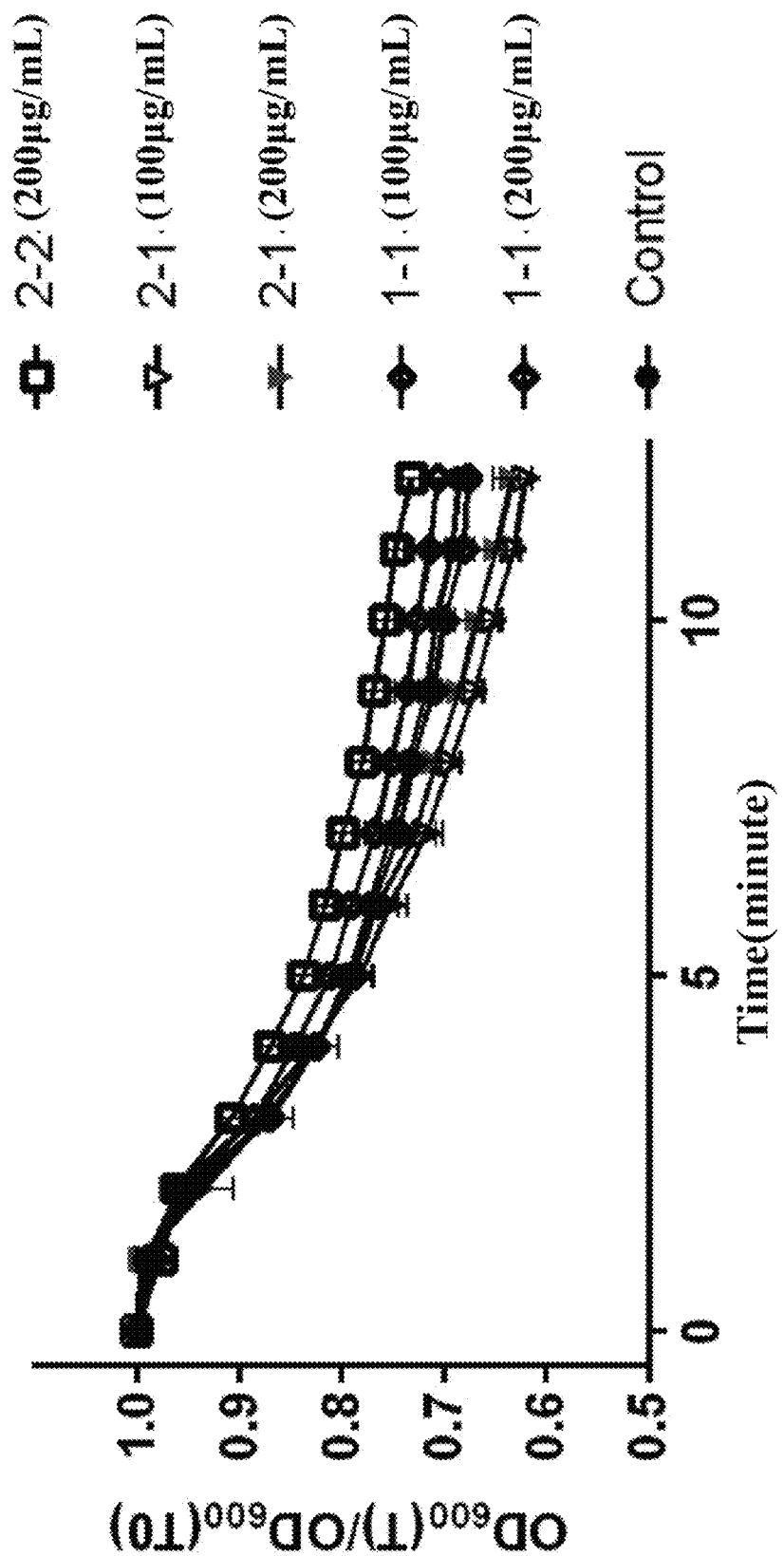
FIG. 6 is a curve diagram illustrating the effect of various Hp phenotypes in different concentration against *Clostridium difficile*.
Figure 7:
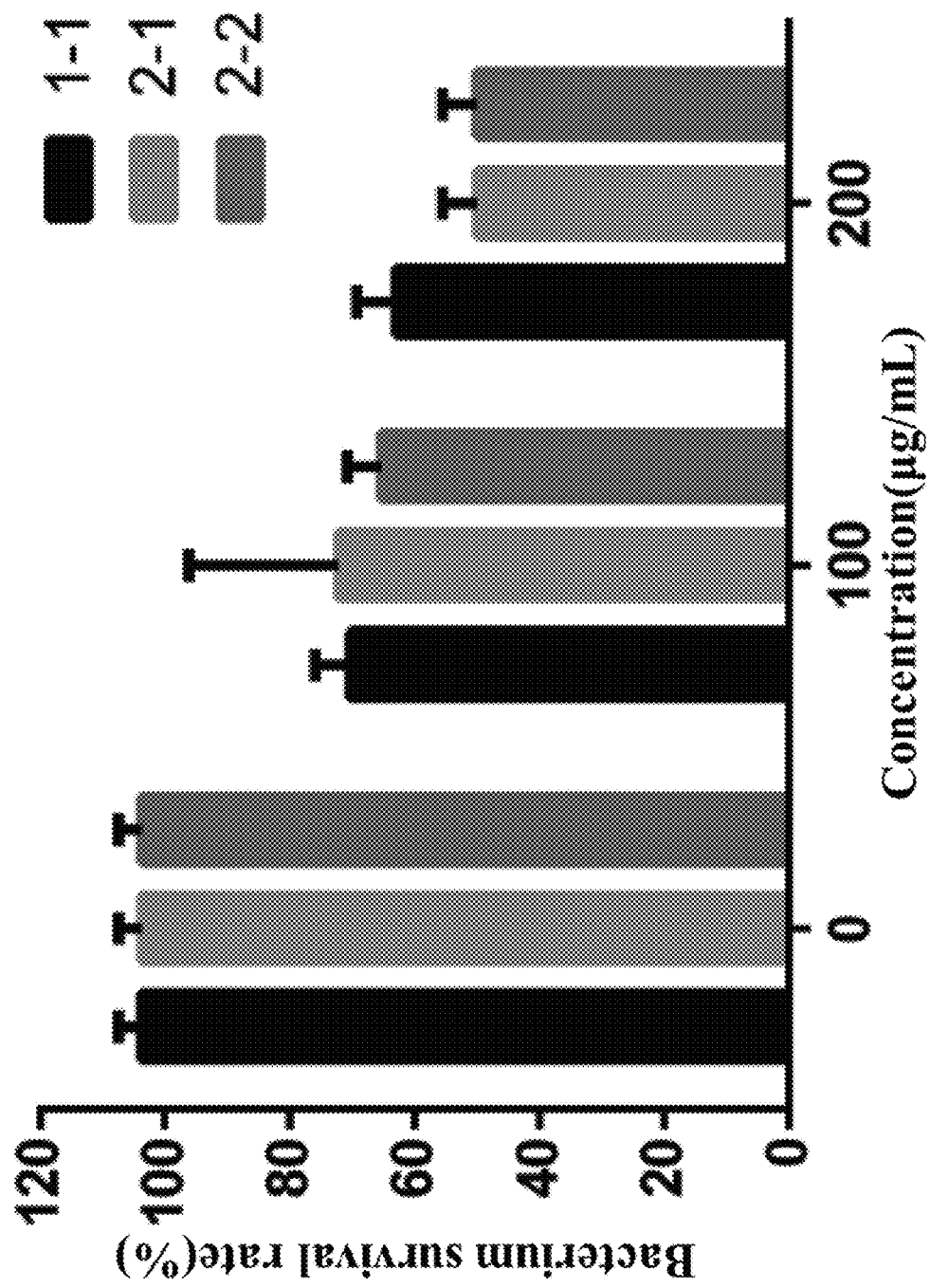
FIG. 7 is a curve diagram the survival rate of *Clostridium difficile* incubated with various Hp phenotypes in different concentration.

As shown in FIGS. 5-7, all Hp phenotypes possess ability against a gram-positive bacterium and a gram-negative bacterium, and the ability is nearly equal to that of the conventional antibiotic, ampicillin or penicillin/streptomycin.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for promoting wound healing, comprising: administering a modified haptoglobin subunit to a subject in need thereof, the modified haptoglobin subunit comprising an amino acid sequence selected from one of SEQ ID NOs: 1-3.

2. The method as claimed in claim 1, wherein the modified haptoglobin subunit is obtained via gene engineering or chemical synthesis.

3. The method as claimed in claim 1, wherein the haptoglobin subunit has an anti-oxidant property and/or an anti-bacterial property.

4. The method as claimed in claim 1, wherein the wound is a chronic wound.

5. The method as claimed in claim 4, wherein the chronic wound is a pressure ulcer, a decubitus ulcer, a leg ulcer, or a diabetic foot ulcer.

* * * * *

SEQUENCE LISTING

<160> NUMBER OF SEQ ID NOS: 3

<210> SEQ ID NO 1
<211> LENGTH: 82
<212> TYPE: PRT
<213> ORGANISM: Artificial Sequence
<220> FEATURE:
<223> OTHER INFORMATION: Synthesized

<400> SEQUENCE: 1

Val Asp Ser Gly Asn Asp Val Thr Asp Ile Ala Asp Gly Ala Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asn Glu Lys Gln Trp Ile Asn Lys Ala Val Gly Asp Lys
    50                  55                  60

Leu Pro Glu Cys Glu Ala Val Ala Gly Lys Asp Lys Asn Pro Ala Asn
65                  70                  75                  80

Pro Val

<210> SEQ ID NO 2
<211> LENGTH: 141
<212> TYPE: PRT
<213> ORGANISM: Artificial Sequence
<220> FEATURE:
<223> OTHER INFORMATION: Synthesized

<400> SEQUENCE: 2

Val Asp Ser Gly Asn Asp Val Thr Asp Ile Ala Asp Gly Ala Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Ala Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
                100                 105                 110

Lys Gln Trp Ile Asn Lys Ala Val Gly Asp Lys Leu Pro Glu Cys Glu
            115                 120                 125

Ala Val Ala Gly Lys Asp Lys Asn Pro Ala Asn Pro Val
        130                 135                 140

<210> SEQ ID NO 3
<211> LENGTH: 245
<212> TYPE: PRT
<213> ORGANISM: Artificial Sequence
<220> FEATURE:
<223> OTHER INFORMATION: Synthesized

<400> SEQUENCE: 3

Ile Leu Gly Gly His Leu Asp Ala Lys Gly Ser Phe Pro Trp Gln Ala
1               5                   10                  15

-continued

```
Lys Met Val Ser His His Asn Leu Thr Thr Gly Ala Thr Leu Ile Asn
            20              25              30

Glu Gln Trp Leu Leu Thr Thr Ala Lys Asn Leu Phe Leu Asn His Ser
            35              40              45

Glu Asn Ala Thr Ala Lys Asp Ile Ala Pro Thr Leu Thr Leu Tyr Val
50              55              60

Gly Lys Lys Gln Leu Val Glu Ile Glu Lys Val Val Leu His Pro Asn
65              70              75              80

Tyr Ser Gln Val Asp Ile Gly Leu Ile Lys Leu Lys Gln Lys Val Ser
            85              90              95

Val Asn Glu Arg Val Met Pro Ile Ala Leu Pro Ser Lys Asp Tyr Ala
            100             105             110

Glu Val Gly Arg Val Gly Tyr Val Ser Gly Trp Gly Arg Asn Ala Asn
            115             120             125

Phe Lys Phe Thr Asp His Leu Lys Tyr Val Met Leu Pro Val Ala Asp
            130             135             140

Gln Asp Gln Cys Ile Arg His Tyr Glu Gly Ser Thr Val Pro Glu Lys
145             150             155             160

Lys Thr Pro Lys Ser Pro Val Gly Val Gln Pro Ile Leu Asn Glu His
            165             170             175

Thr Phe Cys Ala Gly Met Ser Lys Tyr Gln Glu Asp Thr Cys Tyr Gly
            180             185             190

Asp Ala Gly Ser Ala Phe Ala Val His Asp Leu Glu Glu Asp Thr Trp
            195             200             205

Tyr Ala Thr Gly Ile Leu Ser Phe Asp Lys Ser Cys Ala Val Ala Glu
            210             215             220

Tyr Gly Val Tyr Val Lys Val Thr Ser Ile Gln Asp Trp Val Gln Lys
225             230             235             240

Thr Ile Ala Glu Asn
            245
```